United States Patent [19]

Vesterberg

[11] 4,284,491
[45] Aug. 18, 1981

[54] APPARATUS FOR ELECTROPHORESIS

[75] Inventor: Olof Vesterberg, Saltsjö-Duvnäs, Sweden

[73] Assignee: C. Desaga GmbH Nachf. Erich Fecht, Heidelberg, Fed. Rep. of Germany

[21] Appl. No.: 94,307

[22] Filed: Nov. 13, 1979

[30] Foreign Application Priority Data

Nov. 13, 1978 [SE] Sweden .............................. 7811719
Oct. 27, 1979 [DE] Fed. Rep. of Germany ....... 2943541

[51] Int. Cl.³ ...................... B01D 13/02; B01D 57/02
[52] U.S. Cl. ............................ 204/299 R; 204/180 G
[58] Field of Search ............ 204/180 G, 180 S, 299 R; 424/12

[56] References Cited

U.S. PATENT DOCUMENTS 3,576,727  4/1971  Evatt ............................... 204/180 G
3,867,271  2/1975  Hoefer ............................. 204/180 G
4,048,049  9/1977  Hoefer ............................. 204/180 G X Primary Examiner—Donald R. Valentine
Attorney, Agent, or Firm—Wenderoth, Lind & Ponack

[57] ABSTRACT

An electrophoresis device includes first and second electrode vessels for containing buffer solution and adapted to be connected to poles of a direct current source. A plurality of vertical channels containing carrier medium have opposite ends opening into the first and second electrode vessels. At least one of the electrode vessels has a cavity into which commonly open adjacent ends of the channels. A sealing piece is operable to seal in an airtight manner the cavity and thereby the ends of the channels from the interior of the electrode vessel. A connection extends through the sealing piece to the cavity to connect the cavity and the interiors of the channels to a source of overpressure or underpressure.

10 Claims, 2 Drawing Figures

APPARATUS FOR ELECTROPHORESIS

BACKGROUND OF THE INVENTION

The invention relates to a device for conducting electrophoresis for the quantitative determination and-or preparation of chemical substances in essentially vertical channels containing a carrier medium such as a gel, with the opposite ends of the channels opening out into electrode vessels containing buffer solution, the electrode vessels being connected to the poles of a direct current source.

In recent years electrophoresis has been conducted on an increasing scale in horizontal carrier media, because vertical electrophoresis in separate channels has been regarded as involving too much time-consuming handling, in the filling and emptying of the channels and in the subsequent treatment of the carrier media. However, there are advantages to vertical electrophoresis in channels, in particular the possibility of good cooling and the adaptability to large sample volumes.

SUMMARY OF THE INVENTION

The object of the present invention is to create a device of the general type described, in which the drawbacks involving handling of the carrier medium when multiple channels are employed are eliminated, and wherein the novel device has simple design and construction.

For the solution of this object it is proposed that the channels be formed from a group of tubes which are jointly held and supported and which open out into a common cavity with at least one opening, whereby the cavity is sealable and connectable to a source of overpressure or underpressure. An accomplishment of the invention is that a device employing the invention enables simultaneous filling and emptying of the tubes which form the electrophoresis channels.

The tubes are held together, for example, at the top or bottom end by means of a sealing strip which is installable in the boundary of the sealable cavity in a horizontal partition in the electrode vessel. Thus the sealing strip serves, on the one hand, to hold the tubes together in a proximal group, and on the other hand, to hold the tubes jointly in such a position that they open out with their upper and-or lower openings into the corresponding sealable cavity or cavities. The group of tubes is removable as a unit from the electrophoretic device.

A spatially simple arrangement results if the electrode vessels are disposed one inside the other, and at least one cavity is provided as a slot in the wall forming the bottom of the inner electrode vessel, with the top openings of the tubes opening out into the cavity. Under this arrangement the group of tubes can be inserted in the slot in the bottom of the inner electrode vessel with the use of the abovementioned sealing strip, such that the tubes open out into the slot with their top openings. The slot can then be covered with a sealing means on the side opposite the tubes, and in turn the source of overpressure or underpressure can be connected to the sealing means.

Preferably as the tubes lead from the upper cavity into the partition which forms the bottom of the inner electrode vessel they pass through a cooling chamber which adjoins the underside of the partition, and the tubes open out with their bottom openings into a second cavity in the form of a slot in a second partition which forms the bottom of the cooling chamber and is located in the outer electrode vessel. With this design the tubes are thus jointly secured at their top and bottom ends in partitions which are provided as integral parts of the electrophoretic device, whereby a common fluid flow field at overpressure or underpressure can be applied at the top and-or bottom openings of the tubes after the sealing of the cavity or cavities, respectively, in order to enable simultaneous filling and-or emptying of the tubes with carrier medium or the like.

If the sealing strips which hold the tubes together in a group on the top and bottom ends can be installed so as to maintain a tight seal in the cavities associated with the partitions, which cavities are in the form of slots, then a quick and simple replacement of the tube group is enabled.

The installation and replacement of the group of tubes with the aid of these sealing strips which hold the tubes together is further facilitated if the sealing strips are made of an elastic material, e.g. silicone rubber or plastic, and-or if the sealing strip narrow conically in the direction of their side which faces the openings of the tubes.

Another simplified design refinement of the invention is attained by having the inner electrode vessel and the cooling chamber formed as a single unit, which rests on supports positioned in the outer electrode vessel between the partition which forms the bottom of the cooling chamber and the bottom of the outer electrode vessel itself.

Problems with leakage currents in the area of the seal between the tubes and the partitions can be avoided if the cooling liquid used in the cooling chamber has minimal electrical conductivity.

According to another specific refinement of the invention, films or the like are used in conjunction with the sealing strips to cover the openings of the tubes, so that tubes previously filled with carrier medium can be stored for quite a long time. When it is thereafter desired to place the device into use, the films are removed.

Further features, advantages, and application possibilities will appear from the following description of typical embodiments with the aid of the attached drawings. In this connection, the subject of the present invention includes all features which are described and-or are disclosed in the drawings, either explicitly per se or in any useful combination.

DETAILED DESCRIPTION OF THE INVENTION

Figure 1:
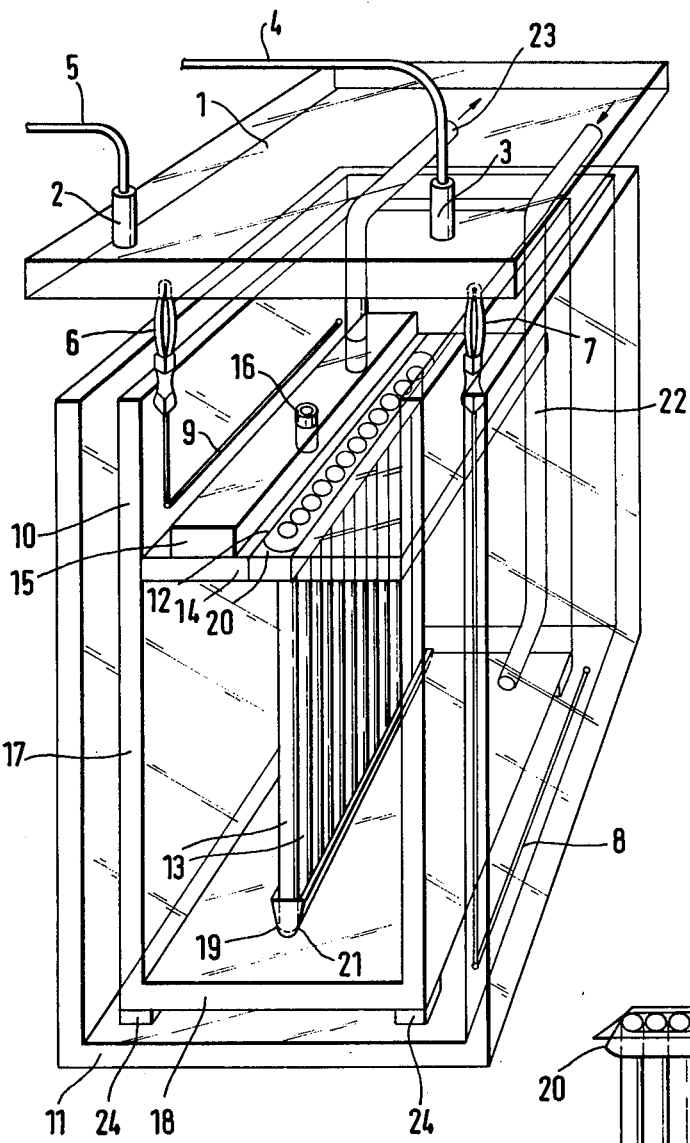
FIG. 1 is a schematic perspective view, basically actual size, of an electrophoretic device employing the invention.

The electrophoretic device of FIG. 1 has an outer electrode vessel 11 for holding a buffer solution, which vessel is furnished with a cover 1. Connector sockets 2 and 3 are mounted on cover 1 and are connectable via conducting wires 4 and 5 to the two poles of a direct current source (not shown). By applying cover 1 an electrical contact is established with plugs 7 and 6 which are held in place in the outer electrode vessel 11 and in an inner electrode vessel 10, respectively, with inner electrode vessel 10 being designed to also be filled with a buffer solution. Plugs 6 and 7 are in electrical communication with electrodes 9 and 8, respectively, at the inner surfaces of the side walls near the respective bottoms of the electrode vessels 10 and 11. Electrodes 8 and 9 are preferably made of platinum wire. Electrode vessels 10 and 11, including cover 1, are preferably made of transparent material such as polymethacrylate or polystyrene. Inner electrode vessel 10 has a cavity 12 in the form of a slot running the length of the bottom of vessel 10, into which cavity the top end of each of vertical tubes 13 opens. Tubes 13 are held together by a sealing strip 20. Tubes 13 are held in place at the areas of opening into the cavity 12 in a watertight seal with the aid of sealing strip 20, which fits into the slot-shaped cavity 12. Sealing strip 20 acts as a lower boundary of cavity 12. The top openings of tubes 13 lie below the top surface of partition 14 which forms the bottom of inner electrode vessel 10. Tubes 13, which are made of glass or plastic, optionally have a diameter in the range from a tenth of a millimeter to several centimeters. Tubes 13 with smaller diameters are used for analytical purposes, and those with larger diameters are used primarily for preparative purposes. Cavity 12, which connects the top openings of tubes 13 with each other, can be sealed in an airtight manner on the top of the cavity with the aid of sealing piece 15 which can be pressed over the surface of partition 14. Sealing piece 15 has therein an opening at which a hose 16 (partially shown), leading to a source of overpressure or underpressure, can be connected. Sealing piece 15 may also be made of transparent plastic. An elastic material such as rubber can be attained to the underside of sealing piece 15, whereby cavity 12 may be given an airtight and watertight seal. For improving the seal; pressure means (not shown) may be applied to press the sealing piece 15 against the partition 14 of the inner electrode vessel 10.

At this point an overpressure or underpressure can be produced in cavity 12 with the aid of the source of overpressure or underpressure. This source of overpressure or underpressure may comprise a piston pump which may be connected to hose 16. Before the electrophoresis operation is carried out, sealing piece 15 is removed from its sealing position, so that a good connection between the buffer solution in electrode vessel 10 and the contents of tubes 13 is established. Also with this maneuver simple charging, from above, of the sample solution which is to be studied into tubes 13 is enabled, while the carrier medium is in the tubes. This can be done using a capillary tube to deliver the sample solution.

The tubes 13 pass from their upper holding place in partition 14 through a cooling chamber 14 which adjoins electrode vessel 10 on the underside of the latter. The tubes 13 are held at their bottom end in the same manner, by a sealing strip 21 which seals them in a cavity 19 which is in the form of a slot in a partition 18 which forms the bottom of cooling chamber 17, so that the bottom openings of the tubes lie within cavity 19.

Figure 2:
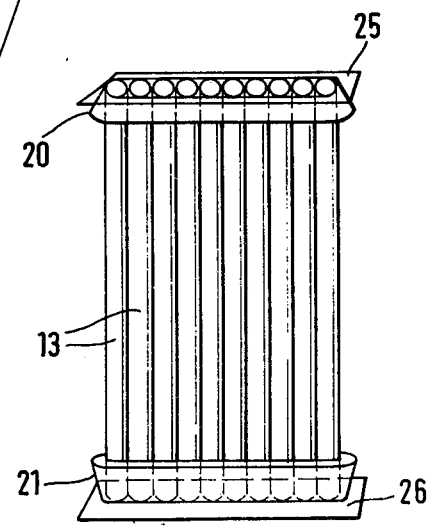
FIG. 2 is a schematic side view of groups of tubes combined with the aid of sealing strips, for use in the device of FIG. 1.

Sealing strips 20 and 21 narrow conically, as seen particularly from FIG. 2, in order to be insertable in simple fashion into cavities 12 and 19, respectively, which cavities are in the form of slots. This conical narrowing is toward the side of the strip nearest the openings of the tubes 13. The strips are made of an elastic material such as silicone rubber or plastic. A sealing piece with hose connection for forming a cavity which may be supplied with overpressure or underpressure, can be applied at the boundary of cavity 19, as was the case with the top cavity 12. The details are not shown, for the sake of ease of viewing and interpretation of the drawings.

Cooling chamber 17 is furnished with an inflow tube 22 which opens at the bottom of chamber 17 and a terminal tube 23 with its intake at the top of chamber 17, for the purpose of circulating a cooling fluid with a minimal electrical conductivity. The low electrical conductivity enables the cooling fluid to serve as an electrical insulator between the inner and outer electrode vessels 10 and 11, thus assisting in avoiding leakage currents at the bottom sealing point of tubes 13 in partition 18 which forms the bottom of cooling chamber 17.

Cooling chamber 17 rests on supports 24 in the outer electrode vessel 11, and carries inner electrode vessel 10 at its top end. Supports 24 can be attached either to the underside of partition 18 which forms the bottom of cooling chamber 17 or to the surface of the bottom of the outer electrode vessel 11. The top edge of outer electrode vessel 11 reaches a height which corresponds approximately to that of the top edge of inner electrode vessel 10. In this way it is possible to maintain the level of the electrode buffer in the two electrode vessels 10 and 11 at approximately the same level, thus enabling the hydrostatic pressure difference across the tubes 13 to be regulated or completely eliminated. This in turn enables the risk of spurious fluid flow of buffer solution through tubes 13 to be avoided, and enables the substances in tubes 13 to be maintained in place. This amounts to an essential advantage over known devices for electrophoresis or isoelectric focusing in agarous gels.

FIG. 2 shows a group of tubes 13 held together by means of top and bottom sealing strips 20 and 21 which, for example, may be made of silicone rubber. These sealing strips may be perforated to match each of the tubes 13, for receiving and holding them. The openings of the tubes 13 and-or of the sealing strips 20 and 21 may be closed off in an airtight manner, using films or the like, 25 and 26, which may also be made of plastic. When the group of tubes is to be used, the films are then removed from the sealing strips 20 and 21. This makes it possible to keep tubes 13 which have been partly filled with, for example, an agarous gel, for several days until they are to be used.

The inventive device is amenable to the conduct of various types of electrophoresis processes, for example isotacho-electrophoresis or isoelectric focusing in materials with density gradients or in the water phase of various carrier media, such as gels from agarose or from polyacrylamide, which are employed to avoid convection interference. It is particularly possible using the inventive device to employ underpressure from the top or overpressure from the bottom, or vice versa, to completely or partially fill the tubes with the solutions. In this manner, for example, gels can be developed in the tubes, in which gels the concentration of the polyacrylamide increases in the downward direction, and decreases corresponding to the pore size. The emptying of the carrier media similarly may be accomplished by means of the application of overpressure and-or underpressure.

In particular, quantitative immunoelectrophoresis may be carried out advantageously with the inventive device in agarose gels in tubes 13, wherein tubes 13 are first partially filled with antibodies against the substance which is to be detected. Then the test solutions are applied to the gel which has been previously produced in tubes 13. During the electrophoresis the substances to be determined migrate downwardly in the gels and produce precipitates the depth of the formation of which in the gels depends on the amount of the substance to be analyzed in the sample solution which was applied. It has been found that the depth of the precipitate is approximately proportional to the amount of substance to be analyzed. Accordingly it is possible to detect the presence of additional substances and to quantify their concentrations provided they interact with materials to form precipitates. Thus, for example, protein A from staphylococci can form precipitates with certain immunoglobulins. Lectins can form precipitates with certain carbohydrates and-or carbohydrate-containing proteins. After the electrophoresis and after the gels are removed from tubes 13 with the aid of overpressure or underpressure, the precipitates can be visibilized, for example by staining. The removal action may be easily accomplished by connecting the underpressure or overpressure to cavity 12 or 19, both of which are in fluid communication with the openings of tubes 13. In the process the gels can be collected onto a special support, e.g. a glass or plastic plate. With gentle pushing out and drawing out of the gels from the tubes 13 the gels will line up in parallel on the support, and can then be fixed by drying. It is also possible to press out or draw out the gels onto a screen and then cover them with a second screen which is rigidly attached to the first. This technique is also advantageous, for example, for polyacrylamide and other gels when they are to be stained before drying or when their enzyme activities are to be tested. This technique avoids mixing up of the different gel bands. The expulsion of the gels from tubes 13 under the conditions that a known sequence is assured facilitates their processing and identification, and provides substantial time savings.

Sometimes it is preferable that the electrophoresis be carried out in the presence of density gradients or in a concentration of agarose which is so low that it is not possible to expel the contents of the tubes 13 in the form of plugs. However, with the inventive device the tubes 13 can be filled and at the same time the solutions in all of them can be removed in these critical cases by suction or by application of pressure, wherewith, for example, a slight pressure excess is produced in upper cavity 12. In all the abovedescribed cases any overpressure can be brought about with the aid of a gas, e.g. air, or a liquid. In this expulsion process the tubes 13 preferably are held over a row of test tubes standing in a rack. This arrangement yields major simplification and savings of time over previously known procedures. The gel is simultaneously expelled from the tubes and collected in a number of separate test tubes.

Heat removal from the gels or density-gradient materials in tubes 13 is very effective because tubes 13, having relatively small diameters, present a comparatively large surface area to the cooling medium in cooling chamber 17. The wall thicknesses of tubes 13 can be made much thinner than the distance between cooling liquid and gel in, for example, horizontal electrophoretic devices of known type.

According to the invention the tubes 13 may have a round or other cross section. They may be made of a plastic material cut from a continuous piece. Also the form of cavities 12 and 19 may vary. Their cross sections need not be rounded off. Their bottom surface may be oval, rectangular, or square.

More detailed illustrations of the device according to the invention appear in the following examples.

EXAMPLE 1

To 3 ml of a 1% (wt per vol) agarose solution in 0.02 M sodium barbitol buffer with pH 8.6 and temperature 55° C. was added 5 $\mu$l canine antiserum against human transferrin (from Dako Immunoglobulines, of Copenhagen). Then the bottom of the tubes was immersed in a trough filled with this solution. With sealing piece 15 in place over slot-shaped cavity 12 and using a syringe, the solution was sucked up into tubes 13 as per FIG. 1, to where the top of the gel solution was about 2 cm below the top edge of the tubes. After the gel set, sealing piece 15 was removed and the unit comprised of inner electrode vessel 10 and cooling chamber 17 was inserted in outer electrode vessel 11. Fifteen $\mu$l human serum was introduced into tubes 13 in dilutions between 1:500 and 1:4000 at intervals of 500 in the divisor, using as the diluent the abovedescribed buffer with 8% sucrose as an additional ingredient contained in the buffer. Electrode-vessels 10 and 11 were filled with the abovedescribed buffer solution to 2 cm below their top edge. Then a voltage of approximately 200 V was applied to electrodes 8 and 9 for approximately an hour. Then the direct current source was disconnected and the unit comprising inner electrode vessel 10 and cooling chamber 17 was removed from outer electrode vessel 11 and the buffer was poured out. Finally the sealing piece 15 was again applied and attached over slot-shaped cavity 12, and a syringe was attached via hose 16. The group of tubes 13 was inclined and held at an incline with their openings over a flat horizontal glass plate. By exerting a pressure using the syringe, the gel was slowly forced out of the individual tubes 13, with associated horizontal movement of the glass plate. The individual gel plugs lay parallel on the plate. Holding the first-exiting gelling material stationary by light pressure on it facilitated the process of bringing it out. The individual gel plugs were then air-dried on the glass plate. Next they were immersed for 60 minutes in a protein stain solution containing 0.5% Coomassie R 250 (sodium deoxynaphthonate from ICI of Manchester, England) in 45% ethanol, 45% water, and 10% acetic acid. The excess stain was removed using the preceding solution but without stain content. For each gel the distance from the edge of sample application to the part of the precipitate with the greatest migration distance was measured. This distance was proportional to the amount of transferrin. In typical cases the correlation coefficient was 0.96. This example shows that the inventive device is suitable for use in the quantitative determination of substances.

EXAMPLE 2

Here also a device according to FIG. 1 was used, but with a tube separation of 5 mm. A density gradient material was prepared with a gradient mixer according to Hilbe and Petterson (Separation Science 1968, 3:535-549), from a less-dense water solution with a content of 5% sucrose and 1% Ampholine (from LKB-Producter, of Sweden) and a more-dense water solution containing 50% sucrose and 1% Ampholine. After slot 19 was closed off with a sealing piece 15 the gradient-forming material was pumped through hose 16 such that the less-dense solution came out on top in each tube 13, with the solution with increasing density underneath. The tubes 13 were filled up to 10 mm below their top edges. Slot-shaped cavity 12 was closed off with another sealing piece 15 and a clamp on hose 16. Next, sealing piece 15 (the second sealing piece) under tubes 13 was removed. The part of the device with the tubes was then set into outer vessel 17, which was filled up to the height of the top side of partition 14 with a 50% aqueous solution containing 0.0001 M phosphoric acid. Following this the top sealing piece 15 was removed. Sample solutions of approximately 1 mg hemoglobin in 10 μl water were then deposited using a capillary pipette directly on top of the solution with the least density in each tube 13. The tubes 13 were then filled up the remainder of the way with 0.001 M sodium hydroxide. Then a direct current source with a potential of 500 V was applied to electrodes 8 and 9 for 18 hours. Thereafter, sealing piece 15 was again placed over slot-shaped cavity 12. A syringe was connected to hose 16. The part of the device which contained the tubes 13 was then positioned over test tubes arranged in a stand, so that each tube 13 was positioned directly over a corresponding test tube. By applying moderate pressure with the aid of the syringe it was possible to slowly divide the contents of tubes 13, moving the test tube rack in intervals whereby tubes 13 were sequentially positioned over new test tubes. In this way the contents of tubes 13 could be divided into the desired number of segments, which number could be chosen freely. The concentration of hemoglobin in each of these segments was then determined by light absorption. The determination of the pH in each segment showed that a pH gradient had been produced in the segments. The main hemoglobin fraction was focused in each tube 13 at a pH of around 7.2. This experiment showed clearly that the filling of multiple tubes, isoelectric focusing, and subsequent division can be carried out easily and reliably with the use of the inventive device.

SUMMARY

In the device for electrophoretic investigations and analyses in essentially vertical channels of which the opposite openings open out into electrode vessels containing buffer solutions, which solutions in turn are connected to the opposite poles of a direct current source, the filling and emptying of the channels is facilitated by having at least one group of tubes with at least one opening opening out into a common cavity, which cavity is sealable with respect to the corresponding electrode vessel and may be connected to a source for producing an overpressure or underpressure in the cavity.

I claim:

1. A device for conducting electrophoresis for the quantitative determination and/or preparation of chemical substances, said device comprising:

first and second electrode vessel means for containing buffer solution and adapted to be connected to poles of a direct current source;
a plurality of substantially vertical channel means for containing carrier medium and having opposite ends opening into said first and second electrode vessel means, first ends of said channel means commonly opening into a cavity;
means for sealing, in an airtight manner, said cavity and thereby said first ends of said channel means from the interior of the respective said electrode vessel means; and
means for connecting said cavity to a source of overpressure or underpressure.

2. A device as claimed in claim 1, wherein said channel means comprise a plurality of jointly held and supported tubes, said cavity is formed in a horizontal partition of said respective electrode vessel means, and further comprising sealing strip means for holding said tubes in said cavity and for defining a boundary of said cavity.

3. A device as claimed in claim 2, wherein said first electrode vessel means is positioned within said second electrode vessel means, said cavity comprises a slot formed in a wall forming the bottom of said first electrode vessel means, and upper ends of said tubes open into said slot.

4. A device as claimed in claim 3, further comprising a cooling chamber positioned between said first and second electrode vessel means, said cooling chamber having a bottom formed by a partition having therein a second slot forming a second cavity, lower ends of said tubes opening into said second cavity, said tubes extending through said cooling chamber.

5. A device as claimed in claim 4, further comprising second sealing strip means for holding said lower ends of said tubes in said second cavity.

6. A device as claimed in claim 5, wherein said sealing strip means comprise elastic material.

7. A device as claimed in claim 5, wherein said sealing strip means narrow conically in directions toward the openings in the respective ends of said tubes.

8. A device as claimed in claim 4, wherein said first electrode vessel means and said cooling chamber are formed as a single unit resting on supports positioned in said second electrode vessel means between a partition forming the bottom of said cooling chamber and the bottom of said second electrode vessel means.

9. A device as claimed in claim 4, wherein said cooling chamber has therein a cooling fluid having a low electrical conductivity.

10. A device as claimed in claim 2, further comprising film means for selectively covering openings of said tubes adjacent said sealing strip means.

* * * * *